(12) United States Patent
Biedermann et al.

(10) Patent No.: US 6,755,870 B1
(45) Date of Patent: Jun. 29, 2004

(54) LEG PROSTHESIS WITH AN ARTIFICIAL KNEE JOINT AND METHOD FOR CONTROLLING A LEG PROSTHESIS

(75) Inventors: Lutz Biedermann, VS-Villingen (DE); Wilfried Matthis, Weiswell (DE); Christian Schulz, Mittweida (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 0 days.

(21) Appl. No.: 09/622,754

(22) PCT Filed: Dec. 22, 1999

(86) PCT No.: PCT/EP99/10280

§ 371 (c)(1),
(2), (4) Date: Aug. 21, 2000

(87) PCT Pub. No.: WO00/38599

PCT Pub. Date: Jul. 6, 2000

(30) Foreign Application Priority Data

Dec. 24, 1998 (DE) .......................... 198 59 931

(51) Int. Cl.[7] .................................. A61F 2/48
(52) U.S. Cl. ....................................... 623/24
(58) Field of Search ............... 623/24, 26, 27, 623/43, 44, 45, 46

(56) References Cited

U.S. PATENT DOCUMENTS 5,383,939 A * 1/1995 James .................. 188/317
5,888,212 A * 3/1999 Petrofsky et al. ............ 623/24

FOREIGN PATENT DOCUMENTS

| DE | 39 09 672 C2 | 10/1989 |
| DE | 69209476 T2 | 3/1996 |
| DE | 19521464 A1 | 3/1997 |
| DE | 19754690 A1 | 7/1999 |
| EP | 0 549 855 A2 | 7/1993 |
| EP | 0 628 296 A2 | 12/1994 |
| FR | 2 623 086 | 5/1989 |
| GB | 1191633 | 5/1970 |
| GB | WO9822727 | * 5/1998 .............. F16F/9/53 |
| WO | WO 99/44547 | 9/1999 |

OTHER PUBLICATIONS

H. Dietl, et al.; "Der Einsatz von Elektronik bei Prothesen zur Versorgung der unteren Extremitat"; Med. Orth. Tech.; 117 (1997) pp. 31–35.

R. Kaitan; "Die Verwendung von Mikrocontrollern in der Prothetik"; Med. Orth. Tech. 117 (1997) pp. 26–30.

Arai, K.I., et al., "Iron Loss of Tertiary Recrystallized Silicon Steel (Invited)", IEEE Transactions on Magnetics, pp. 3949–3954 (1989).

* cited by examiner

Primary Examiner—David J. Isabella
Assistant Examiner—William H Matthews
(74) Attorney, Agent, or Firm—George W. Neuner; Edwards & Angell, LLP

(57) ABSTRACT

There is provided a leg prosthesis, comprising a thigh portion (1) and a lower leg portion (2) both being connected by a knee joint (3), said knee joint (3) comprising a damping element (6) for controlling the knee joint movement, and means (S1) for detecting the knee angle and means (S4–S7; S8, S8', S9, S9') for detecting the force acting on the prosthesis; and a control unit for controlling said damping element (6) as a function of the detected values of said knee angle and said force; and an adjustment device (10) adjusting the control of said damping element according to the type of gait and as a function of detected values of said knee angle and said force.

19 Claims, 5 Drawing Sheets

LEG PROSTHESIS WITH AN ARTIFICIAL KNEE JOINT AND METHOD FOR CONTROLLING A LEG PROSTHESIS

The invention relates to a leg prosthesis with an artificial knee joint according to the preamble of claim 1 and a method for controlling a leg prosthesis according to the preamble of claim 14.

When walking with a prosthesis, the prosthesis upper leg is moved by the leg stump in a forward direction during the walking. If the damping is not adapted, due to its inertia, the lower leg may be angled to a very large extent. The person wearing the prosthesis then has to wait until the prosthesis has moved back to its forward position before being able to place its foot on the ground. This results in unharmonic gait appearance, inappropriate timing performance and thus poor or less than optimal support properties.

There are known leg prostheses with an artificial knee joint where a damping element in the form of a pneumatic or hydraulic cylinder is provided for swing phase control and as a so-called fall back brake. The adaptation of the leg prosthesis to the person carrying it is achieved using a stationary gait analysis system. To this end, the person wearing the prosthesis has to perform a test walk with the prosthesis, e.g. on a running machine, with an orthopedic technician then providing a subjective judgement of the gait appearance. Together with the subjective feelings of the person wearing the prosthesis, the various components of the prosthesis are then adapted and set. Very often, the result of the setting is inaccurate, since the setting is carried out using subjective criteria. In addition, supplementary modifications such as weight, temperatures or the nature of the ground are not taken into consideration.

Further, the known damping elements for artificial knee joints have the drawback of not being able to respond fast enough to an abrupt change of the gait dynamics.

GB 1,191,633 discloses a leg prosthesis having an artificial knee joint with a hydraulically controlled brake, where a ferro-colloidal liquid or another magnetic liquid are used as the hydraulic liquid.

DE 195 21 464 A1 discloses a leg prosthesis having an artificial knee joint according to the preamble of claim 1 and a method for controlling such prosthesis according to the preamble of claim 14. In this leg prosthesis, when the type of gait is changed, the control of the knee brake can also be changed using a respective adaptation of a stored reference pattern. To various types of gait such as walking on flat ground or climbing stairs is associated a special control program, respectively, for controlling the knee brake. During the walking, the type of gait is determined by measuring the hip joint muscular activity and comparing the measured values with stored reference values, and the knee brake is controlled with the control program associated to this type of gait. The reference values for a type of gait are determined beforehand for each person wearing the prosthesis. However, there is no change of a control program associated to a specific type of gait.

In the known leg prosthesis, however, there is the problem that an adaptation of the prosthesis control, i.e. of the control programs, to changing circumstances with respect to the person wearing the prosthesis, such as gain or loss of weight of the person wearing the prosthesis or wearing different shoes, or with respect to the surroundings such as walking on flat ground on a bumpy path, is not carried out.

It is an object of the invention to provide a leg prosthesis having an artificial knee joint and a method for controlling such prosthesis, guaranteeing an optimum operation of the prosthesis and adapted to the person wearing it irrespective of changing operational circumstances as well as a fast reaction to abrupt changes in gait dynamics.

This object is achieved by a leg prosthesis according to claim 1 and by a method according to claim 14 for controlling such prosthesis. Further embodiments of the invention are presented in the dependent claims.

Additional features and purposes of the invention will be understood from the description of embodiments with reference to the figures where:

Figure 1:
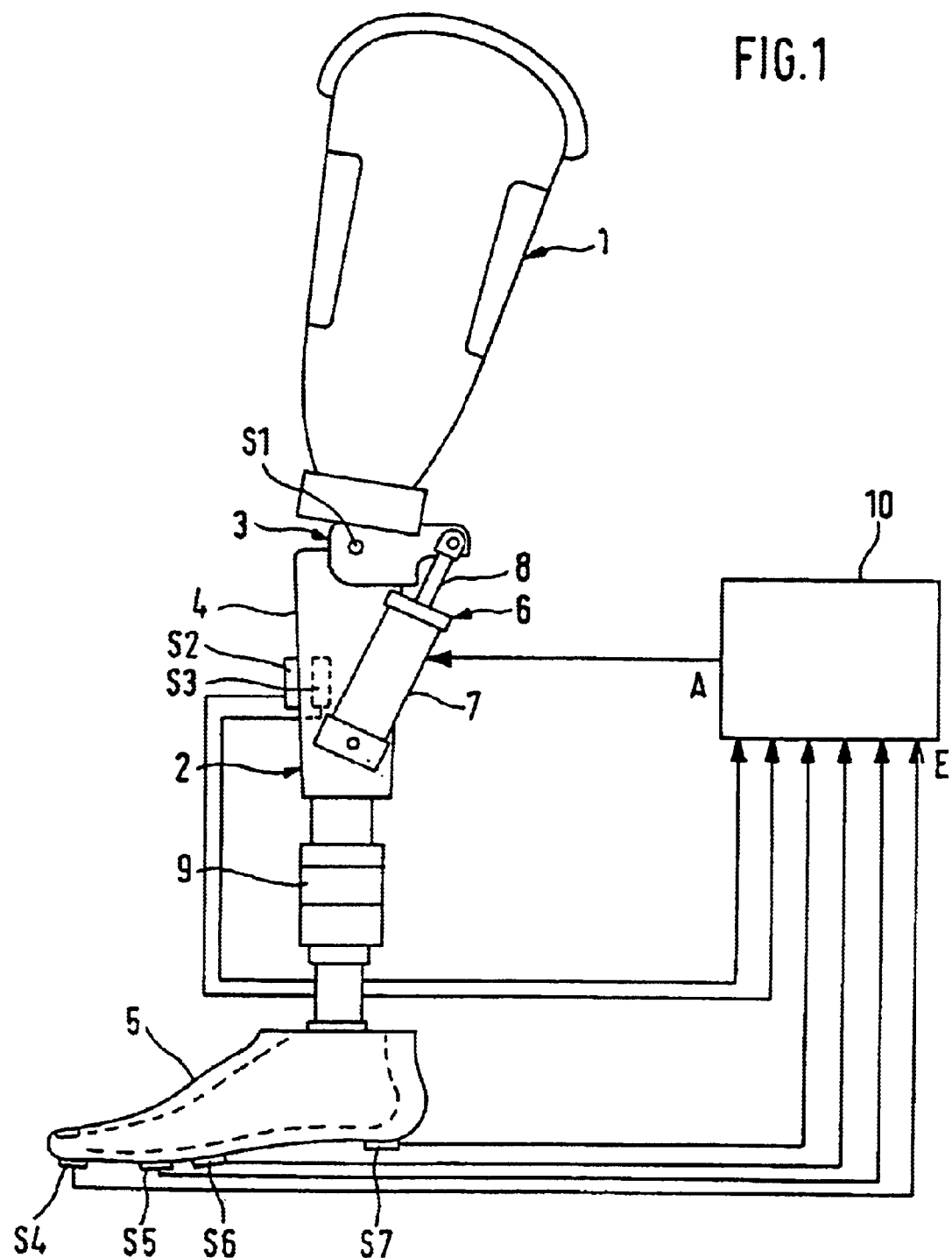
FIG. 1 is a schematic representation of a first embodiment of a leg prosthesis having an artificial knee joint with swing phase control and a fall back brake.

Referring in particular to FIG. 1, the leg prosthesis comprises a thigh portion 1 and a lower leg portion 2 as well as a knee joint 3 connecting the two portions. The lower leg portion 2 comprises a shin-bone part 4 having a lower leg tube 9 and a foot part 5 connected therewith. The foot part 5 comprises a leaf spring in a known fashion, not shown in the figure, permitting resilient stepping on the ground. The thigh portion 1 is designed to be connected to the leg stump.

The knee joint 3 comprises a damping element in the form of a hydraulic piston-cylinder means 6. The cylinder 7 of the piston-cylinder means 6 is connected to the shin-bone part 4 and the piston rod 8 of the piston-cylinder means 6 is connected to the knee joint 3. Preferably, the cylinder 7 is an MRF-cylinder. This cylinder is filled with a magneto-rheological liquid (MR-liquid) having the property of changing its viscosity within a range of 3 to 5 milliseconds under the influence of a magnetic field. The magneto-rheological liquid consists of a suspension of magnetizable particles in the micrometer range in an oil.

The piston 8 or the cylinder 7 of the piston-cylinder means 6 further comprises a solenoid which can be controlled by an external signal and which provides the magnetic field for acting on the magneto-rheological liquid.

The leg prosthesis further comprises a number of sensors for measuring motion and force. In the knee joint 3, there is provided a knee angle sensor S1 for detecting the knee angle. At the shin-bone part 4, acceleration detectors are optionally provided. A frontally arranged acceleration sensor S2 is supposed to measure the acceleration in the direction of propagation, a laterally arranged acceleration sensor S3 is supposed to measure the acceleration perpendicular to the direction of propagation. As these acceleration sensors, regular acceleration sensors such as those known from automotive technology, may be used.

For measuring the force acting on the prosthesis, one or more force sensors are provided. According to the embodiment shown in FIG. 1, force sensors S4 to S7 are provided in the region of the sole of the foot. The force sensor S4 is arranged in the toe region, the force sensors S5 and S6 are arranged in the bale region, and a force sensor S7 is arranged in the heel region. As these sensors, regular force sensors such as those based on a compression spring, may be used. The force sensors provide information for the introduced force and permit to distinguish between standing phase and swing phase.

Figure 2A:
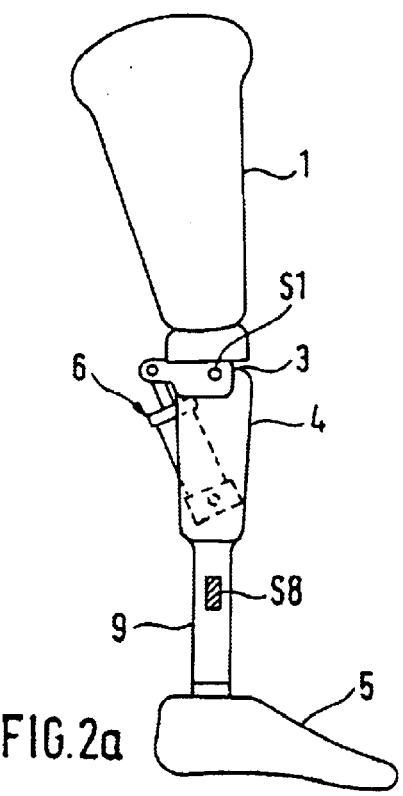
FIG. 2(a) is a lateral view of a leg prosthesis in a second embodiment.
Figure 2B:
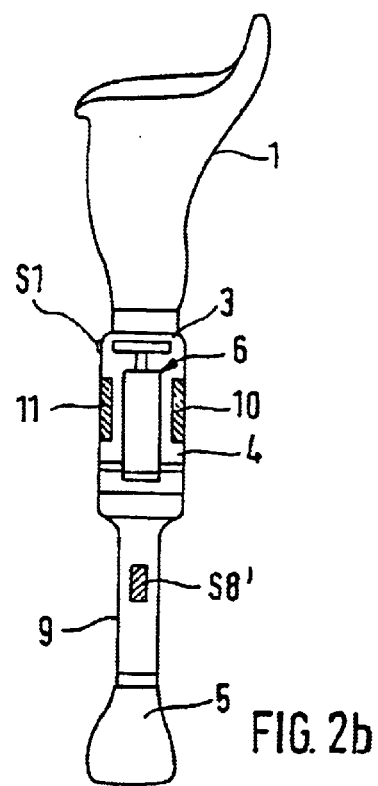
FIG. 2(b) is a front view of the leg prosthesis of FIG. 2(a)

FIGS. 2(a) and 2(b) show a preferred embodiment of the leg prosthesis where force sensors S8 and S8' are provided at the lower leg tube 9. For example, the force sensors are strain gauge sensors. In the operating position of the leg prosthesis, the force sensor S8 is provided laterally either inside or outside and detects the total force acting on the prosthesis. In the operating position of the leg prosthesis, the force sensor S8' is provided at the front or at the rear side and detects the bending occurring at the lower leg tube.

Figure 3A:
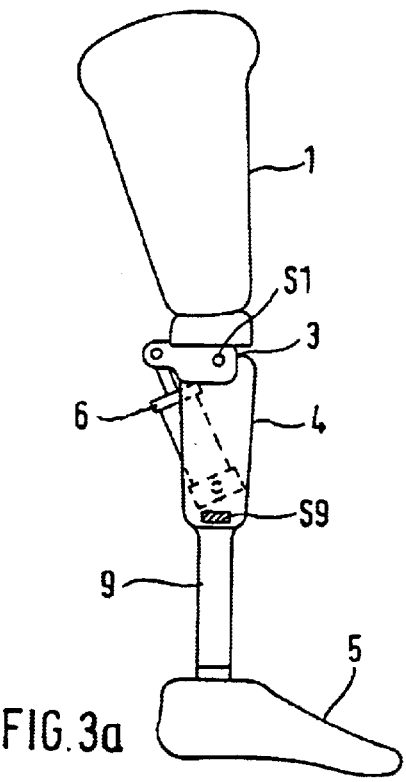
FIG. 3(a) is a lateral view of a third embodiment of a leg prosthesis.
Figure 3B:
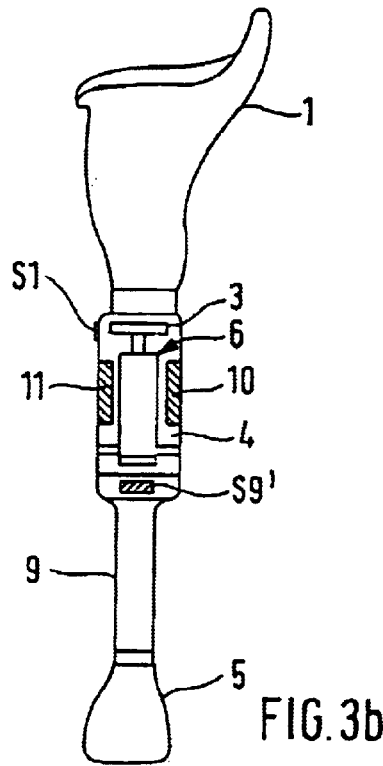
FIG. 3(b) is a front view of the leg prosthesis of FIG. 3(a)

In FIGS. 3(a) and 3(b), a further preferred embodiment of the leg prosthesis is shown where, as an alternative to the previously described embodiment, force sensors S9 and S9' are integrated in the shin-bone part 4 for measuring the total force and the lateral (bending) force, respectively. Preferably, the force sensors S9, S9' are formed as strain gauge type sensors embedded into the carbon fiber support material of the shin-bone part 4. The arrangement of the sensors S9 and S9' in the operation position of the leg prosthesis is such that the sensor S9 is provided laterally either at the inside or at the outside and the sensor S9' at the rear side or the front side, i.e. analagous to the embodiment according to FIGS. 2(a) and 2(b).

Compared to the arrangement of force sensors in the foot part 5, the arrangement of the force sensors in the lower leg tube 9 or in the shin-bone part 4 has the advantage that different foot parts may be used, if required, and that no inconvenient wires for transferring data to the foot part to the control unit of the prosthesis are present.

The signal outputs of sensors S1 to S7 and of S1 and S8, 8' or S9, 9' are connected to one or more inputs E of a control and adjustment unit 10. Preferably, the control and adjustment unit 10 is integrated in the shin-bone part 4, as described in FIGS. 2(b) and 3(b). In addition, a battery 11 is integrated in the shin-bone part 4 or in the lower leg tube 9, providing power to the control and adjustment unit 10. The control unit comprises a CPU and a data memory. In the data memory, a program having an algorithm for processing the incoming signals from the sensors and for generating one or more output signals is provided. A signal output A of the control unit 10 is connected to the piston-cylinder means 6 and in particular to the solenoid provided in the piston.

Figure 4:
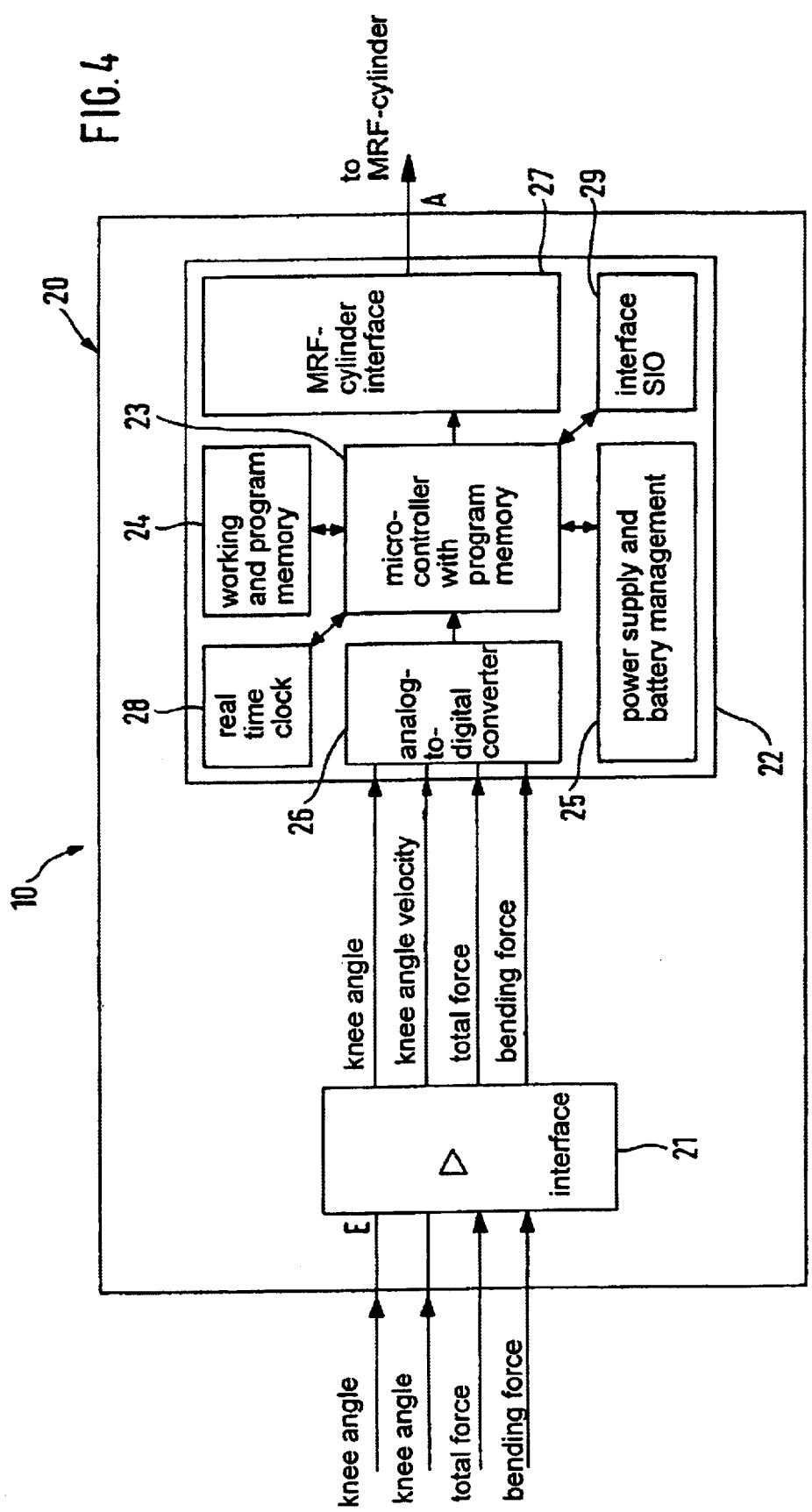
FIG. 4 is a schematic representation of a control and adjustment device for the leg prosthesis according to the invention.

The configuration of the control and adjustment unit 10 can be seen from FIG. 4 and will be described in more detail. The components for processing the signals generated by the sensors are arranged on a circuit board 20. The circuit board 20 comprises an interface 21 where the signals detected by the sensors are applied in accordance with the knee angle, the total force or the ground reaction force and the bending force. In a further embodiment, the signals of the acceleration sensors can also be entered. The interface 21 is formed such that preprocessing such as amplification of the signals occurs and a knee angular velocity is calculated. In addition, an electronic circuit 22 is provided on the circuit board 20, which circuit comprises a micro-controller 23 having a program memory, a working and parameter memory 24, a power supply 25, an analog-to-digital converter 26 and an interface 27 as the interface for the piston-cylinder means 6. Optionally, a real time clock 28 and an SIO-interface 29 are provided. There are provided corresponding connecting lines between the individual components of the circuit. The signals "knee angle, knee angular velocity, total force and bending force" preprocessed in the interface 21 are fed into the analog-to-digital converter 26 and the generated digital signals are fed into the micro-controller 23. In the micro-controller 23, an algorithm for predetermined processing of the signals is stored. The signals output from the micro-controller are applied to the interface 27 and output for controlling the piston-cylinder means.

Figure 6:
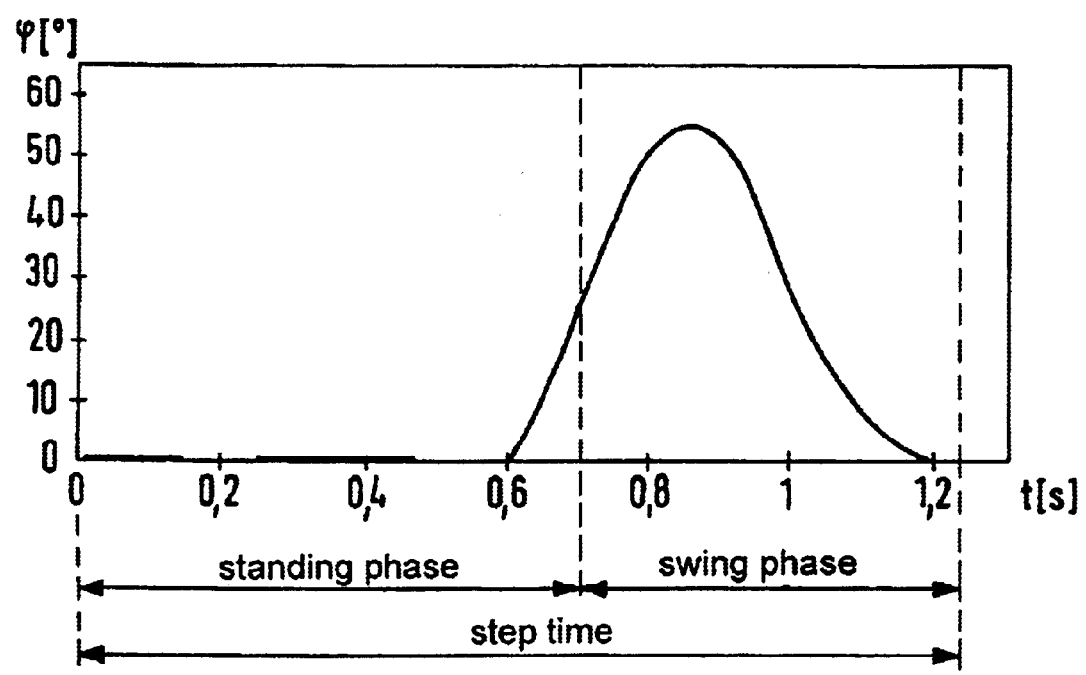
FIG. 6 is a curve representing the knee angle as a function of time for a step.

In the working and parameter memory 24 and the program memory of the micro-controller 23, the following data are stored:

a) A knee angle reference curve represented in FIG. 6 and illustrating the knee angle as a function of time for the time of one step. The knee angle reference curve is composed of the standing phase which is the time comprising putting the heel on the ground via rolling the foot around the bale until the beginning of the flexion of the knee joint, and a swing phase which comprises the flexion and the extension of the knee joint until again placing the heel on the ground. The knee angle reference curve shows optimum step performance where the values for the knee angle have been empirically determined. The knee angle reference curve is the same for every person wearing the prosthesis. Preferably, the knee angle reference curve is stored in normalized form such as a step time of 1 second.

For each type of gait such as walking on an incline which contains walking horizontally as a special case, or for climbing stairs, such knee angle reference curve identical for whoever wears the prosthesis is stored.

b) An allocation of knee angle maxima for different gait velocities. Discrete values of the knee angle maximum with respect to an empirical gait velocity have been determined empirically beforehand for each person wearing the prosthesis or are simply given without knowing the person currently wearing the prosthesis. Intermediate values can be obtained by interpolation.

c) Control parameters P for controlling the piston-cylinder means for different gait velocities, respectively. The control parameters comprise an extension damping gain factor Ed which is a measure of the damping gain for the extension, and a flexion damping gain factor Fd which is a measure of the damping gain for the flexion. These control parameters P have been determined empirically beforehand for each person wearing the prosthesis for different gait velocities and using a gait analysis, or are simply given as starting values for controlling the piston-cylinder means without having been adapted already to a specific person wearing the prosthesis.

The predetermined algorithm stored in the micro-controller 23 for storing and adjusting the piston-cylinder means will be described with reference to FIG. 5. The algorithm constitutes the method according to the invention for controlling and adjusting the control unit of the leg prosthesis.

Based on the digital signals output from the analog-to-digital converter 26 for the knee angle, the knee angular velocity, the total force and the bending force, the following step values are determined in step (1):

the maximum flexion angle corresponding to the maximum knee angle for this step;

the stretch lead time which is the time between the extension stop and the placing of the heel on the ground;

the standing time; and the step time.

Based on these step values, the maximum flexion angle and the stretch lead time are determined as actual step values.

At the same time, the presumed step velocity is determined in step (1). For example, this is done by combining an initiation time which is the time starting from the introduction of the force and the first change in knee angle until complete lift-off from the ground, and the introduction knee angle. As an alternative, the step velocity is determined by determining the knee angle velocity at a predetermined flexion angle, preferably at about 20°, at which angle the foot is lifted off completely from the ground.

In step (2), the actual step values are compared to the set step values. The set step values are step values empirically determined by gait analysis for optimum prosthesis setting to achieve natural gait performance and are identical for every person wearing the prosthesis. In particular, the set step values are as follows:

The knee angle maximum is preferably between 55° and 60°. The stretch lead time is preferably in the range of 0.06 to 0.1 seconds.

The set step values for a particular type of gait correspond to the step values determined from the knee angle reference curve for this type or gait. Thus, the set step values include a basic shape and a course of time, but not the absolute values.

In step (3), a combination of the differences between set step values and actual step values is performed for the determined step velocity in a predetermined fashion in order to determine correction factors for the control parameters P:

a) If the maximum actual flexion angle is in the range of the set knee angle, a correction is not required. If the maximum actual flexion angle is greater or less than the set knee angle, the flexion damping gain factor Fd has to be increased and decreased, respectively.

b) If the actual stretch lead time is in the range of the set stretch lead time, a correction is not required. If the actual stretch lead time is greater or less than the set stretch lead time, the extension damping gain factor Ed has to be increased and decreased, respectively.

c) If the rest time is greater than 2 seconds, the step is not to be included in the readjustment of the control parameters, since it characterizes starting or stopping when walking.

The extent of the increase or decrease of the correction factors can be constant in modulus, i.e. independent of the amount of difference between the actual step values and the set step values, or it may depend on the difference between the actual step values and the set step values.

In step (4), the control parameters P are selected for controlling the piston-cylinder means as a function of the presumed step velocity and of the corresponding value for the knee angle maximum stored in the working and program memory 24. In accordance with the result from step (3), the control parameters P are combined with correction factors and thus, are readjusted vis-a-vis the empirically determined original control parameters P stored in the memory for the corresponding velocity. The corrected actual control parameters P' thus obtained are again stored in the memory as values now valid and will be used as a starting point in the subsequent step for readjustment.

The part of the algorithm performing the actual level control of the piston-cylinder means operates as described below:

The actual control parameters P' are used for controlling flexion and extension, respectively, i.e. they effect a defined setting of the damping or brake value of the piston-cylinder means between a basic damping an a maximum damping. The control of the piston-cylinder means is firmly given for the knee angle reference curve. In order to determine when the calculated and corrected control parameters P' are supposed to become effective, the knee angle reference curve is scaled to the presumed step velocity. When controlling flexion, the maximum flexion angle and the flexion time are adapted, and when controlling extension, an adaptation to the obtained maximum flexion angle and the required flexion time is effected. Flexion control is only performed in the time interval between stopping and reaching the maximum knee angle. A difference is established between the actual knee angle velocity and the required velocity in order to reach the next knee angle position in the time interval. If the actual knee angle velocity is too large, damping has to be performed. In the case of flexion, the damping is equal to the difference in velocity times the flexion damping gain factor. In the case of extension, damping is equal to the difference in velocity times the extension damping gain factor. If the actual velocity is too small, damping is not performed.

Figure 5:
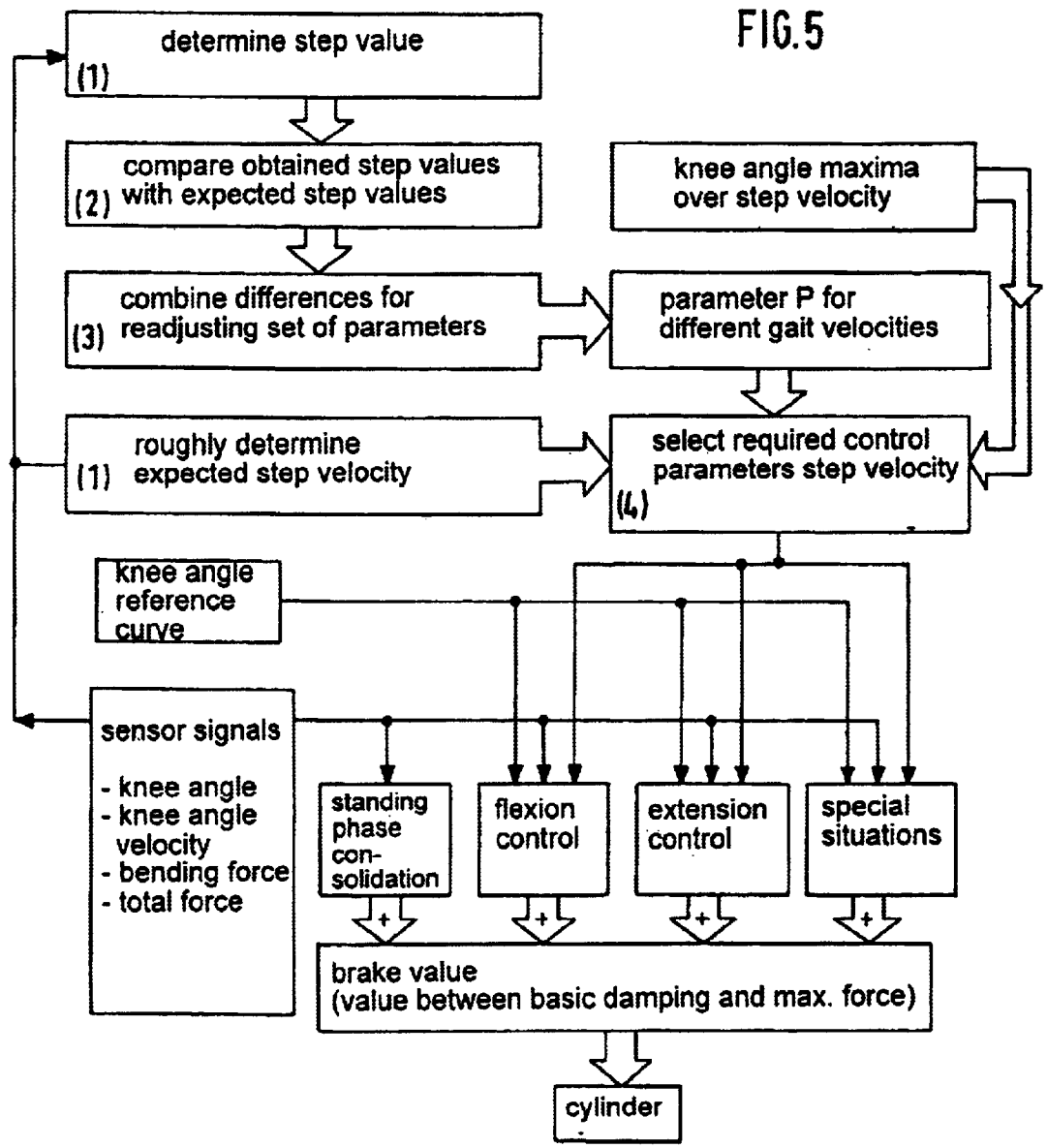
FIG. 5 is a diagram for illustrating the operation of the control and the adjustment for the leg prosthesis according to the invention.

As can be seen from FIG. 5, the partial step of step (1) in which the presumed step velocity is determined, and step (4) with the subsequent control of the piston-cylinder means constitute the control plane. The partial step (1) in which the step values are determined, together with steps (2) and (3) constitutes the adjustment plane.

The control and adjustment through the algorithm also contains a standing phase consolidation. To this end, the signals "total force" and "bending force" are used. If, in the stepping-on-the-ground interval, the total force increases and the bending is in the heel region or the knee angle increases and the total force acts on the foot while the bending force is not in the front foot region, the brake will be activated by 100%, i.e. no further flexion can be performed. However, if the bending force is in the front foot region, the brake will not be activated.

The control of special situations comprises the controls "climbing stairs", "stumbling" and "falling down". Walking on an incline is treated like extension or flexion. For the special situation "climbing stairs", there are separate empirical values, i.e. a special knee angle reference curve. For the special situations "stumbling" and "falling down" or "hitting", the standing phase consolidation is activated.

In operation, the control of the leg prosthesis works as follows. The measuring data of the knee angle and force sensors are fed to the control unit 10. The control unit 10 generates control signals for and feeds them to the piston-cylinder means as a function of the measuring data. As a function of the measuring data, the solenoid generates a defined magnetic field causing a specific change in viscosity of the magneto-rheological liquid in cylinder 7. By changing the viscosity, the depth of penetration of piston 8 into cylinder 7 and thus the damping can be controlled accordingly. The change in damping occurs within about 3 to 5 milliseconds. This is of particular advantage when using the damping as a fall back brake. When the person wearing the prosthesis stumbles, the damping thus immediately built up can prevent at an early time the lower leg portion from being folded together.

The control unit, the sensors and the damping element are connected to each other in a feed back control circuit, as described, i.e. the damping is set during the walking by readjusting the control parameters P for setting the damping based on given values for the control parameters P. Compared to a traditional prosthesis control, this provides the advantage that the setting of the prosthesis functions is effected directly as a function of the natural gait performance of the person wearing the prosthesis.

In particular, the described leg prosthesis using the described algorithm has the advantage that the prosthesis is not controlled by selecting a defined gait performance out of a multitude of previously determined gait performances for a person wearing the prosthesis, but that a readjustment of the predetermined values for a defined gait performance is carried out. Thus, the prosthesis flexibly adapts to the instantaneous gait performance and a nearly natural gait is possible. In addition, readjusting the control parameters for different velocities enables the prosthesis control to be adapted to modified circumstances such as a change in weight of the person wearing the prosthesis or the use of a different foot part or a different shoe.

Modified embodiments are conceivable. More or fewer sensors than the sensors described above may be provided.

Instead of a piston-cylinder means having a piston that can be axially displaced within the cylinder, a piston-cylinder means having a rotating piston may also be used, which piston may be equipped with blades exposed to a specific resistance in the cylinder as a function of the viscosity of the magneto-rheological liquid. In this case, the piston rod is connected to a rotating shaft of the knee joint.

Nevertheless, the invention is not limited to a leg prosthesis having a hydraulic cylinder with a magneto-rheological liquid as the damping element. Rather, regular hydraulic cylinders may be used as well, where the damping can be adjusted using a bypass valve between the chambers. In this case, the valve opening may be controlled by stepping motors.

What is claimed is:

1. A leg prosthesis comprising:

a thigh portion;

a lower leg portion;

a knee joint connecting the thigh portion and the lower leg portion so that a knee angle is formed between the thigh portion and the lower leg portion;

said knee joint comprising a damping element for controlling the knee joint movement, angle detection means for detecting the knee angle and force detection means for detecting a force acting on the prosthesis;

a control unit for controlling said damping element as a function of the detected values of said knee angle and said force; and an adjusting device;

wherein the control unit is structured and arranged to control said damping element as a function of control parameters (P) previously stored for different gait velocities; and the adjustment device is structured and arranged to select a control parameter (P) from said previously stored control parameters as a function of the type of gait and the detected values of said knee angle and said force, to change the selected control parameter (P) to a value (P') equal to or different from the previously stored value as a function of the type of gait and the detected values of said knee angle and said force, to store the changed control parameter (P') instead of the selected control parameter (P), and to use the changed control parameter (P') as a starting point in a subsequent step.

2. The leg prosthesis in accord with claim 1, wherein said adjustment device is structured and arranged to change the selected control parameter (P) from the previously stored value under the condition that actual step values that are determined from said detected values differ from set step values predetermined in advance that are set identically for each person wearing the prosthesis.

3. The leg prosthesis in accord with claim 2, wherein said predetermined set step values comprise maximum knee angle and a stretch lead time which is the time between an extension stop and the placing of the heel during a step.

4. A leg prosthesis in accord with claim 2, wherein the adjustment device is structured and arranged in such a way that, starting from each of the instantaneously valid values for said control parameters (P) within a step period, it changes said control parameters (P) as a function of the detected values for said knee angle and said force such that a difference between said actual step values and said predetermined set step values corresponding to an optimized type of gait is minimized.

5. The leg prosthesis in accord with claim 1, wherein said damping element is a magneto-rheological fluid cylinder.

6. The leg prosthesis in accord with claim 1, wherein said angle detection means comprises a knee angle sensor provided in said knee joint.

7. The leg prosthesis in accord with claim 1, wherein the lower leg portion comprises a shin-bone part and a lower leg tube, and wherein said force detection means comprises at least two force sensors provided in said lower leg tube.

8. The leg prosthesis in accord with claim 1, wherein the lower leg portion comprises a shin-bone part, and wherein at least two force sensors are provided in said shin-bone part.

9. The leg prosthesis in accord with claim 8, wherein said shin-bone part comprises a material, and said two force sensors are strain gauge sensors, which are integrated into said material of said shin-bone part.

10. The leg prosthesis in accord with claim 1, wherein said adjustment device is provided at said lower leg portion of the leg prosthesis.

11. A leg prosthesis in accord with claim 1, wherein the adjusting device minimizes changes in control of the damping element as a function of a detected value of the knee angle and of the force to correspond to an optimized type of gait.

12. A leg prosthesis comprising:

a thigh portion;

a lower leg portion;

a knee joint connecting the thigh portion and the lower leg portion so that a knee angle is formed between the thigh portion and the lower leg portion;

said knee joint comprising a damping element for controlling the knee joint movement, angle detection means for detecting the knee angle and force detection means for detecting a force acting on the prosthesis;

a control unit for controlling said damping element as a function of the detected values of said knee angle and force; and an adjusting device;

wherein the control unit is structured and arranged to control said damping element as a function of control parameters (P) previously determined for different gait velocities;

the adjustment device is structured and arranged to readjust said control parameters as a function of the type of gait and the detected values of said knee angle and said force;

said adjustment device is structured and arranged to readjust the parameters under the condition that actual step values that are determined from said detected values differ from set step values predetermined in advance that are set identically for each person wearing the prosthesis;

said predetermined set step values comprise a maximum knee angle and a stretch lead time which is the time between an extension stop and the placing of the heel during a step; and the maximum knee angle is between 55° and 60°.

13. A leg prosthesis comprising:

a thigh portion;

a lower leg portion;

a knee joint connecting the thigh portion and the lower leg portion so that a knee angle is formed between the thigh portion and the lower leg portion;

said knee joint comprising a damping element for controlling the knee joint movement, angle detection means for detecting the knee angle and force detection means for detecting a force acting on the prosthesis;

a control unit for controlling said damping element as a function of the detected values of said knee angle and said force; and an adjusting device;

wherein the control unit is structured and arranged to control said damping element as a function of control parameters (P) previously determined for different gait velocities;

the adjustment device is structured and arranged to readjust said control parameters as a function of the type of gait and the detected values of said knee angle and said force;

said adjustment device is structured and arranged to readjust the parameters under the condition that actual step values that are determined from said detected values differ from set step values predetermined in advance that are set identically for each person wearing the prosthesis;

said predetermined set step values comprise a maximum knee angle and a stretch lead time which is the time between an extension stop and the placing of the heel during a step; and the stretch lead time is between 0.06 and 0.1 seconds.

14. A leg prosthesis comprising:

a thigh portion;

a lower leg portion;

a knee joint connecting the thigh portion and the lower leg portion so that a knee angle is formed between the thigh portion and the lower leg portion;

said knee joint comprising a damping element for controlling the knee joint movement, angle detection means for detecting the knee angle and force detection means for detecting a force acting on the prosthesis;

a control unit for controlling said damping element as a function of the detected values of said knee angle and said force; and an adjusting device;

wherein the control unit is structured and arranged to control said damping element as a function of control parameters (P) previously determined for different gait velocities;

the adjustment device is structured and arranged to readjust said control parameters as a function of the type of gait and the detected values of said knee angle and said force; and the control parameters (P) includes an extension damping gain factor (Ed) and a flexion damping gain factor (Fd), and wherein the damping element is adjusted to a predetermined damping value for the cases of extension or flexion as a function thereof, respectively.

15. A leg prosthesis comprising:

a thigh portion;

a lower leg portion;

a knee joint connecting the thigh portion and the lower leg portion so that a knee angle is formed between the thigh portion and the lower leg portion;

said knee joint comprising a damping element for controlling the knee joint movement, angle detection means for detecting the knee angle and force detection means for detecting a force acting on the prosthesis;

a control unit for controlling said damping element as a function of the detected values of said knee angle and said force; and an adjusting device;

wherein the control unit is structured and arranged to control said damping element as a function of control parameters (P) previously determined for different gait velocities;

the adjustment device is structured and arranged to readjust said control parameters as a function of the type of gait and the detected values of said knee angle and said force; and said force detection means comprises total force detection means for detecting the total force acting on the prosthesis and lateral force detection means for detecting the lateral force on the prosthesis.

16. A method for controlling a leg prosthesis comprising a thigh portion; a lower leg portion; a knee joint connecting the thigh portion and the lower leg portion so that a knee angle is formed between the thigh portion and the lower leg portion, said knee joint comprising a damping element for controlling the knee joint movement, angle detection means for detecting the knee angle and force detection means for detecting a force acting on the prosthesis; a control unit for controlling said damping element as a function of the detected values of said knee angle and said force; and an adjustment device;

wherein the control unit is structured and arranged to control said damping element as a function of control parameters (P) previously stored for different gait velocities and the adjustment device is structured and arranged to readjust the parameters as a function of the type of gait; said method comprising:

repeatedly detecting values of said knee angle and said force, selecting a control parameter (P) from said previously stored control parameters as a function of the type of gait and the detected values of said knee angle and said force, controlling said damping element as a function of the selected control parameter (P), changing the selected control parameter (P) to a value (P') equal to or different from the previously determined value as a function of the type of gait and the detected values of said knee angle and said force; and storing the changed control parameter (P') instead of the selected control parameter (P).

17. The method as set forth in claim 16, wherein during each step with the prosthesis the method further comprises:

determining an expected step velocity;

determining actual step values characterizing the instantaneous type of gait from said detected values;

comparing the actual step values with set step values predetermined in advance; and changing the control parameters as a function of the result of comparing said actual step values with said predetermined set step values.

18. The method as set forth in claim 17, wherein said predetermined set step values comprise a maximum knee angle and a stretch lead time, which is the time between an extension stop and the placing of the heel during a step, and wherein the ranges for the set step values are the same for every person wearing the prosthesis.

19. A method for controlling a leg prosthesis comprising a thigh portion; a lower leg portion; a knee joint connecting the thigh portion and the lower leg portion so that a knee angle is formed between the thigh portion and the lower leg portion, said knee joint comprising a damping element for controlling the knee joint movement, angle detection means for detecting the knee angle and force detection means for detecting a force acting on the prosthesis; a control unit for controlling said damping element as a function of the detected values of said knee angle and said force; and an adjustment device;

wherein the control unit is structured and arranged to control said damping element as a function of control parameters (P) previously determined for different gait velocities and the adjustment device is structured and arranged to readjust the parameters as a function of the type of gait;

said method comprising detecting values of said knee angle and said force and controlling said damping element as a function of the detected values of said knee angle and said force;

said method further comprising during each step with the prosthesis:

determining an expected step velocity;

determining actual step values characterizing the instantaneous type of gait from said detected values;

comparing the actual step values with set step values predetermined in advance; and changing the control parameters as a function of the result of comparing said actual step values with said predetermined set step values;

wherein said predetermined set step values comprise a maximum knee angle and a stretch lead time, which is the time between an extension stop and the placing of the heel during a step, and wherein the ranges for the set step values are the same for every person wearing the prosthesis; and wherein the maximum knee angle is between 55° and 60° and the stretch lead time is between 0.06 and 0.1 seconds.

* * * * *

UNITED STATES PATENT AND TRADEMARK OFFICE
CERTIFICATE OF CORRECTION

PATENT NO. : 6,755,870 B1
DATED : June 29, 2004
INVENTOR(S) : Lutz Biedermann et al.

It is certified that error appears in the above-identified patent and that said Letters Patent is hereby corrected as shown below:

<u>Title page</u>,
Item [75], Inventors, change "Wilfried Matthis, Weiswell (DE)" to -- Wilfried Matthis, Weisweil, (DE) --.

Signed and Sealed this

Seventh Day of September, 2004

JON W. DUDAS
*Director of the United States Patent and Trademark Office*